United States Patent [19]

Shirafuji et al.

[11] Patent Number: 4,849,551
[45] Date of Patent: Jul. 18, 1989

[54] METHOD FOR SEPARATING CYCLOHEXANOL

[75] Inventors: Tamio Shirafuji; Itaru Kawata, both of Niihama, Japan

[73] Assignee: Sumitomo Chemical Company, Limited, Osaka, Japan

[21] Appl. No.: 172,385

[22] Filed: Mar. 24, 1988

[30] Foreign Application Priority Data

Apr. 7, 1987 [JP] Japan .................................. 62-86587

[51] Int. Cl.⁴ ....................... C07C 27/26; C07C 29/74
[52] U.S. Cl. .................................. 568/913; 568/895; 568/899
[58] Field of Search ................ 568/895, 899, 913, 894

[56] References Cited

U.S. PATENT DOCUMENTS 4,187,152  2/1980  Roth, Jr. et al. .................... 568/835
4,469,905  9/1984  Inwood et al. ...................... 568/899
4,691,064  9/1987  Shirafuji et al. .................... 568/835
4,716,253  12/1987 Shirafuji et al. .................... 568/835

FOREIGN PATENT DOCUMENTS 56-43227  4/1981  Japan .
2103033   5/1987  Japan ................................. 568/835
3083034   4/1988  Japan ................................. 568/835

*Primary Examiner*—Werren B. Lone
*Attorney, Agent, or Firm*—Stevens, Davis, Miller & Mosher

[57] ABSTRACT

An industrially excellent method for separating cyclohexanol which comprises carrying out the hydration of cyclohexane in the presence of an acid, and bringing the reaction solution into contact with a mixed solution of a hydrocarbon and phenol to extraction-separate cyclohexanol from the reaction solution.

5 Claims, No Drawings

METHOD FOR SEPARATING CYCLOHEXANOL

The present invention relates to a method for separating cyclohexanol from its aqueous acid solution.

More particularly, the present invention relates to a method for separating cyclohexanol from the reaction solution after carrying out the hydration of cyclohexene in the presence of an acid.

Usually, when cyclohexanol is obtained by the hydration of cyclohexene, the reaction is carried out in the presence of an acid. However, when soluble acids, for example aromatic sulfonic acids, etc. are used, the aqueous solution needs to be of high concentration (JP-B-43-16125), and the greater part of cyclohexanol, a reaction product, is present in this aqueous acid solution of high concentration.

A bond between cyclohexanol present in this aqueous acid solution of high concentration and the acid is so much strong that it is not easy to separate cyclohexanol from the reaction solution.

Hitherto, for separating cyclohexanol from the reaction solution, a method of distilling the reaction solution is known (JP-A-56-43227).

Also, there is a method wherein, after neutralizing the acid with a base, cyclohexanol is extraction-separated with an organic solvent.

In the distillation method, cyclohexanol and water form an azeotropic mixture, and yet the cyclohexanol to water weight ratio of the mixture is 0.2 or less, so that a large amount of water should be distilled out. Consequently, a large quantity of heat is required. Further, because the solubility of cyclohexanol in water is 3.6% by weight at 20° C., treatment such as extraction with organic solvents, etc. becomes again necessary after distillation in order to separate cyclohexanol. The distillation method is therefore economically very disadvantageous.

The method of carrying out extraction-separation with organic solvents after neutralizing the acid in the reaction solution, because of the acid concentration being high, needs a large amount of a base for neutralization. Further, it is usually very difficult industrially to regenerate and recover the formed salt as the acid.

Also, both the methods discharge a large amount of waste water, so that much labor and time are necessary for treatment thereafter.

There is a great demand, therefore, for the appearance of a simple method for separating cyclohexanol from the reaction solution wherein cyclohexene has been hydrated in the presence of an acid.

In view of this situation, the present inventors made an extensive study with an object of separating cyclohexanol easily and economically from the reaction solution containing an acid such as aromatic sulfonic acids, etc., and as a result, completed the present invention.

The present invention provides a method for separating cyclohexanol which comprises carrying out the hydration of cyclohexene in the presence of an acid, and bringing the reaction solution into contact with a mixed solution of a hydrocarbon and a phenol to extraction-separate cyclohexanol from the reaction solution.

Production of cyclohexanol is attained by the hydration of cyclohexene which is carried out by heating cyclohexene in the presence of an acid such as aromatic sulfonic acids, etc.

The resulting reaction solution is separated into a cyclohexene phase and an aqueous solution phase, and the latter phase, as it is or diluted with water, is brought into contact with a mixed solution of a hydrocarbon and a phenol to extraction-separate cyclohexanol from the aqueous acid solution.

In extracting cyclohexanol, the cyclohexanol extraction efficiency increases with decreasing acid concentration of the aqueous acid solution, but a too low concentration is not preferred because the separated and recovered aqueous acid solution needs to be concentrated when it is reused for hydration, which requires a large quantity of heat.

It is therefore preferred that the acid concentration of the aqueous acid solution is regulated in advance with water or low-concentration aqueous acid solution so that it is in a range of from about 30% to about 70% by weight (calculated exclusive of organic substance).

Extraction of cyclohexanol shown in the present invention can be carried out with a hydrocarbon only, but its efficiency markedly increases by mixing a phenol.

By the use of a phenol only, the aqueous solution after hydration does not separate, in many cases, into two phases of a cyclohexanol-containing phase and aqueous acid phase.

The hydrocarbons used include aromatic hydrocarbons, straight-chain aliphatic hydrocarbons, branched aliphatic hydrocarbons and alicyclic hydrocarbons. Of these, aromatic hydrocarbons and alicyclic hydrocarbons are preferred, and benzene, toluene, xylene, tetralin and cyclohexene are particularly preferred. These hydrocarbons may be used in combination.

The phenols include phenol and substituted phenols, being a compound having one or more hydroxyl groups directly bonded to the aromatic ring.

Specifically, there are given phenol, cresol, xylenol, trimethylphenol, ethylphenol, iso-propylphenol, tert-butylphenol, phenylphenol, chlorophenol, nitrophenol, salicylic acid, 2-naphthol, pyrocatechol, etc. These phenols also may be used in combination.

The amount of the mixed solution of a hydrocarbon and a phenol is from about 0.05 to about 5 parts by weight, preferably from 0.1 to 1 part by weight based on 1 part by weight of the aqueous solution after hydration, in terms of the cyclohexanol extraction efficiency.

As to the mixing ratio of a hydrocarbon and a phenol, the amount of a phenol is from about 0.1 to about 2 parts by weight based on 1 part by weight of a hydrocarbon, because there is a necessity to separate the extraction solvent from the aqueous solution after hydration in two phases.

The extraction temperature is not particularly limited, and the extraction efficiency increases with increasing temperature. However, a too high temperature returns cyclohexanol to cyclohexene during extraction, so that a temperature of from room temperature to about 200° C. is usually used.

As to the contact time of the extraction solvent with the aqueous acid solution, even a very short period of time of several minutes is sufficient for extraction-separation.

The separated extraction solvent phase and aqueous acid solution phase are treated by the following means: The extraction solvent phase contains an extremely small amount of the acid which has moved from the other phase, but the acid can easily be recovered by washing with a small amount of water. Thereafter, cyclohexanol can be separated by distillation. While the aqueous acid solution phase contains small amounts of the hydrocarbon and phenol which have moved from the other phase, it can be reused as it is for hydration.

According to the method of the present invention, cyclohexanol can efficiently be extraction-separated from a reaction solution wherein cyclohexene has been hydrated in the presence of an acid, using a mixed solution of a hydrocarbon and a phenol. Consequently, the method of the present invention is an industrially excellent method.

The present invention will be illustrated specifically with reference to the following examples, but it is not limited to these examples.

Hereupon, the extraction rate of cyclohexanol shown in the examples is given by the following equation:

$$\text{Extraction rate of cyclohexanol (\%)} = \left( \frac{\text{amount of cyclohexanol in extraction solvent}}{\text{total amount of cyclohexanol after extraction}} \right) \times 100$$

EXAMPLE 1

To a 200-ml flask was added 40 g of an aqueous solution after hydration containing 45% by weight of p-toluenesulfonic acid and 9% by weight of cyclohexanol.

30 Grams of benzene and 10 g of 2, 6-xylenol were added to the aqueous solution, followed by stirring at 70° C. for 1 hour.

After allowing to stand still for about 30 seconds, the resulting solution was separated into two phases, and cyclohexanol in the extraction solvent was analyzed by gas chromatography to find that the extraction rate of cyclohexanol was 52%.

COMPARATIVE EXAMPLE 1

The procedure was carried out in the same manner as in Example 1 except that 40 g of benzene only was used as the extraction solvent, to find that the extraction rate of cyclohexanol was 44%.

EXAMPLES 2 TO 4 AND COMPARATIVE EXAMPLE 2

40 Grams of an aqueous solution after hydration containing 40% by weight of 2-naphtholsulfonic acid and 9% by weight of cyclohexanol, 6 g of benzene and a prescribed amount of m-cresol were mixed and stirred at 70° C., and after liquid-liquid separation, cyclohexanol in the extraction solvent was analyzed. The results are shown in Table 1.

TABLE 1

| No. | Amount of m-cresol (g) | Extraction rate of cyclohexanol (%) |
|---|---|---|
| Comparative example 2 | 0 | 26 |
| Example 2 | 2 | 43 |
| Example 3 | 4 | 54 |
| Example 4 | 6 | 62 |

EXAMPLES 5 AND 6 AND COMPARATIVE EXAMPLE 3

40 Grams of an aqueous solution after hydration containing 40% by weight of 2-naphtholsulfonic acid and 9% by weight of cyclohexanol, 6 g of cyclohexene and a prescribed amount of m-cresol were mixed and stirred at 70° C., and after liquid-liquid separation, cyclohexanol in the extraction solvent was analyzed. The results are shown in Table 2.

TABLE 2

| No. | Amount of m-cresol (g) | Extraction rate of cyclohexanol (%) |
|---|---|---|
| Comparative example 3 | 0 | 20 |
| Example 5 | 3 | 52 |
| Example 6 | 6 | 62 |

EXAMPLES 7 TO 10 AND COMPARATIVE EXAMPLE 4

To 40 g of an aqueous solution after hydration containing 40% by weight of 2-naphtholsulfonic acid and 9% by weight of cyclohexanol were added 30 g of benzene and 10 g of a phenol or no phenol. The resulting mixture was stirred at 70° C., and after liquid-liquid separation, cyclohexanol in the extraction solvent was analyzed. The results are shown in Table 3.

TABLE 3

| No. | Phenols | Extraction rate of cyclohexanol (%) |
|---|---|---|
| Comparative example 4 | None | 75 |
| Example 7 | o-Cresol | 90 |
| Example 8 | p-Cresol | 89 |
| Example 9 | Tert-butylphenol | 90 |
| Example 10 | 2,6-Xylenol | 86 |

What is claimed is:

1. A method for separating cyclohexanol which comprises carrying out the hydration of cyclohexene in the presence of an acid, and bringing the reaction solution into contact with a mixed solution of at least on member selected from the group consisting of benzene, toluene, xylene, tetralin and cyclohexene and at least one member selected from the group consisting of phenol, cresol, xylenol and tert-butylphenol at a temperature of from room temperature to about 200° C. to extraction-separate cyclohexanol from the reaction solution.

2. A method according to claim 1, wherein the acid is an aromatic sulfonic acid.

3. A method according to claim 1, wherein the acid concentration of the reaction solution to be brought into contact with the mixed solution of a hydrocarbon and a phenol is from 30 to 70%.

4. A method according to claim 1, wherein the mixed solution comprises a hydrocarbon and a phenol of from 0.1 to 2 parts by weight based on 1 part by weight of the former.

5. A method according to claim 1, wherein the amount of the mixed solution of a hydrocarbon and a phenol is from 0.05 to 5 parts by weight based on 1 part by weight of the aqueous reaction solution.

* * * * *